United States Patent [19]

Porter

[11] Patent Number: 5,498,522
[45] Date of Patent: Mar. 12, 1996

[54] METHODS FOR THE USE OF SPERMIDINE/SPERMINE $N^1$-ACETYLTRANSFERASE AS A PROGNOSTIC INDICATOR AND/OR A TUMOR RESPONSE MARKER

[75] Inventor: Carl W. Porter, East Aurora, N.Y.

[73] Assignee: Health Research, Inc., Buffalo, N.Y.

[21] Appl. No.: 153,300

[22] Filed: Nov. 16, 1993

Related U.S. Application Data

[63] Continuation-in-part of Ser. No. 875,091, Apr. 28, 1992, abandoned.

[51] Int. Cl.$^6$ ............................. A61K 49/00; C12Q 1/02; C12Q 1/48; C12Q 1/68; G01N 33/573
[52] U.S. Cl. ...................... 435/6; 435/7.1; 435/7.4; 435/15; 435/91.1; 435/91.2; 435/810; 435/29; 530/387.1; 536/22.1; 514/674
[58] Field of Search ................... 435/6, 7.4, 15, 435/91.1, 91.2, 7.1, 810, 29; 424/9; 530/387.1; 536/22.1

[56] References Cited

PUBLICATIONS

Bernacki, R. et al. Cancer Research 52:2424–2430, 1992.
Porter, C. et al. Cancer Research 53:581–586, 1993.
Gerner, E. et al. Biochem. J. 294:491–495, 1993.
Obayashi, M. et al. Biochem. et Bioph. Acta 1131:41–46, 1992.
Ovejera, A. et al. Annals of Clinical & Laboratory Science 8(1):50–51, 1978.
Casero, R. et al. J. Biol. Chem. 266(2):810–814, 1991.
Casero, R. et al. Biochem. J. 270:615–620, 1990.
Pegg, A. et al. Biochem. J. 267:331–338, 1990.

*Primary Examiner*—W. Gary Jones
*Assistant Examiner*—Paul B. Tran
*Attorney, Agent, or Firm*—Hodgson, Russ, Andrews, Woods & Goodyear

[57] ABSTRACT

Disclosed is a method that relates to the measurement of determinants related to the in-vivo induction of spermidine/spermine $N^1$-acetyltransferase (SSAT), subsequent to polyamine analog treatment (such as with a bis-ethyl spermine analog) of human malignant solid tumor types responsive to the polyamine analog. The method comprises the measurement of one or more SSAT-specific determinants that include SSAT enzyme activity, SSAT enzyme protein, and SSAT m-RNA transcripts. Alternatively, other determinants related to the SSAT induction may be measured. Such determinants include SSAT co-factor acetylCoenzyme A, and SSAT products $N^1$-acetylspermidine and $N^1$-acetylspermine. Measurements of these determinants may be useful as prognostic indicia and tumor response markers to evaluate the clinical effectiveness of anticancer agents comprising polyamine analogs.

35 Claims, 9 Drawing Sheets

Melanoma Cell Line

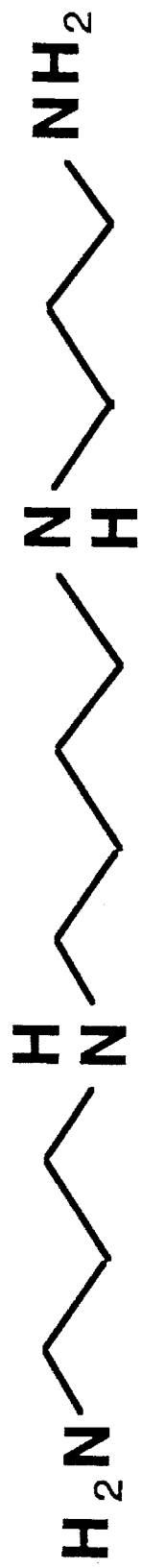
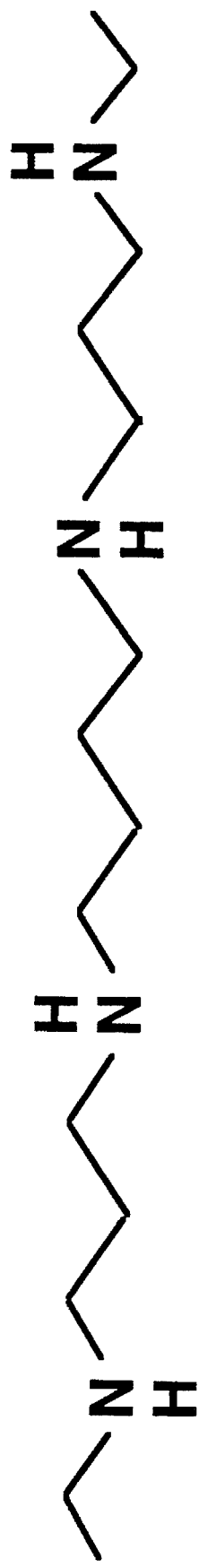
Spermine
$N^1, N^{12}$ - Bis (ethyl) spermine
FIG. 1

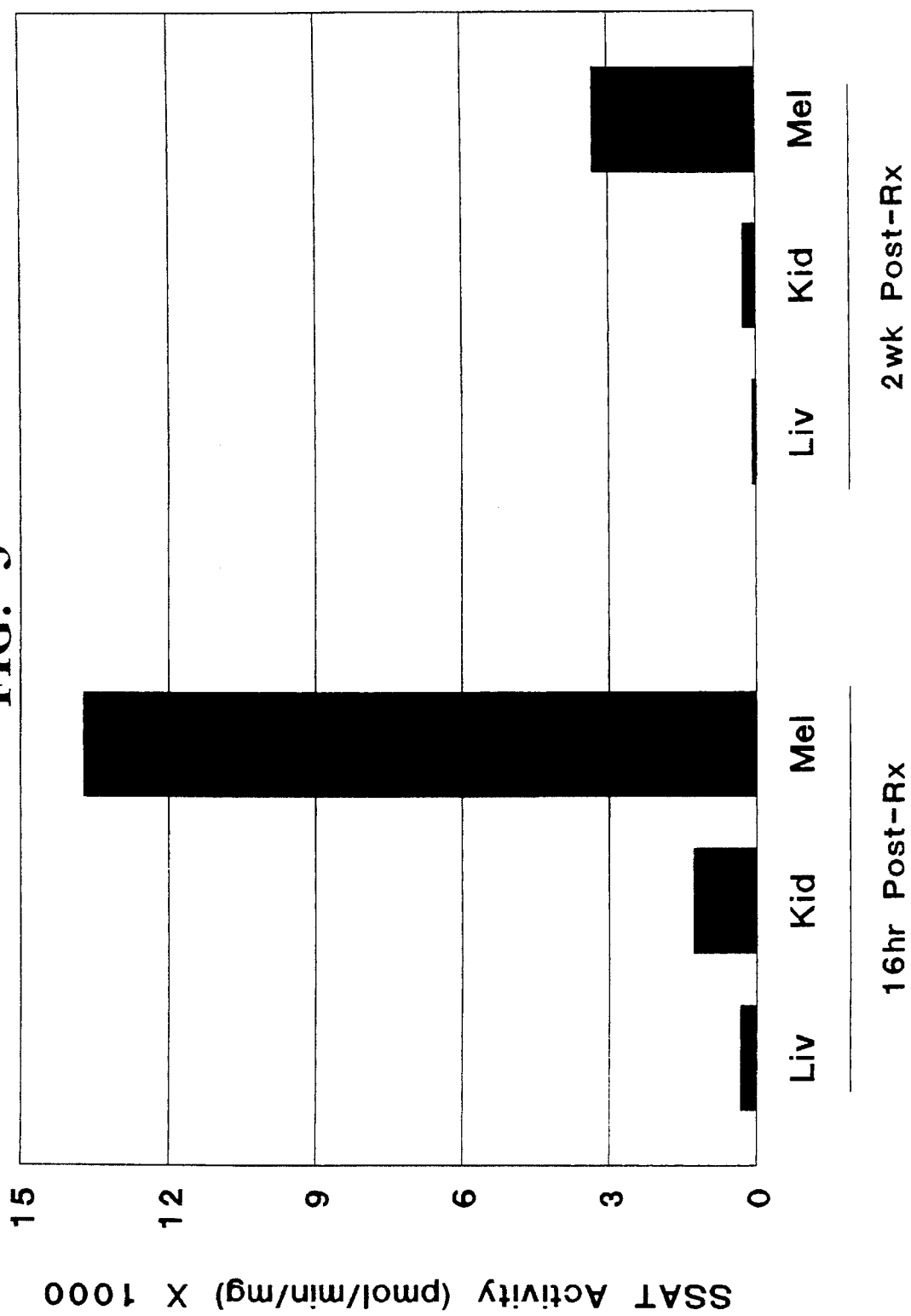

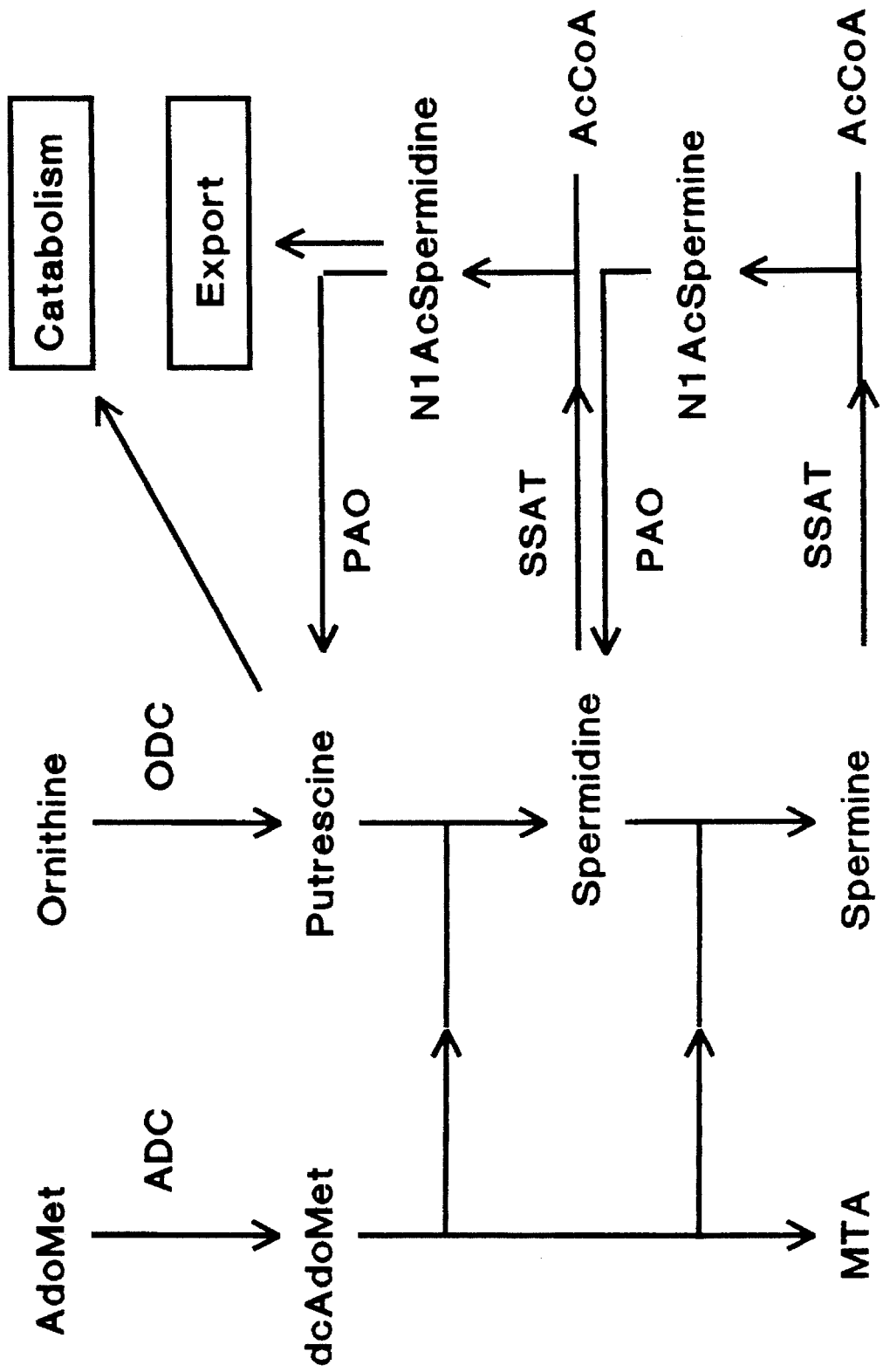

METHODS FOR THE USE OF SPERMIDINE/SPERMINE N¹-ACETYLTRANSFERASE AS A PROGNOSTIC INDICATOR AND/OR A TUMOR RESPONSE MARKER

This invention was made with government support under grant numbers CA-51524, CA-37606, CA-13038, and CA-16056, awarded by the National Cancer Institute. The government has certain rights in this invention.

CROSS REFERENCE TO RELATED APPLICATIONS

This application is a continuation-in-part of U.S. Ser. No. 07/875,091, filed Apr. 28, 1992, now abandoned, which is herein incorporated by reference.

BACKGROUND OF THE INVENTION

1 Field of the Invention

The present invention relates generally to the detection of enzyme levels that are affected by a specific class of cancer chemotherapeutic agents, and more particularly, to the use of the enzyme spermidine/spermine $N^1$-acetyltransferase as a prognostic indicator and/or tumor response marker to facilitate clinical use of the class of anticancer agents that cause induction of the enzyme as a significant part of their biological effect profile.

2 Description of the Background and Related Art

The biological polyamines, putresine, spermidine and spermine are natural components of all mammalian cell types and are known to be essential for cell growth. While their precise role in supporting cell growth is uncertain, it is believed to involve interaction with nucleic acids. These substances and their key biosynthetic enzymes, ornithine and S-adenosylmethionine decarboxylase (ODC and SAMDC, respectively), are increased in neoplastic tissues. Depletion of intracellular polyamine pools unequivocally inhibits cell growth under in-vitro conditions. Therefore, polyamine biosynthesis has been targeted in the development of experimental anticancer strategies.

Because inhibitors of polyamine biosynthetic enzymes lower the polyamine content of tumor cells, they are among the compounds being evaluated for use as anticancer agents. Thus far, these inhibitors have not lead to clinically effective anticancer agents. One of the problems confronting their use is that as soon as polyamine pools are lowered, the key biosynthetic enzymes ODC and SAMDC, as well as polyamine transport, undergo a compensatory increase in activity (Porter et al., 1992, in *Polyamines in the Gastrointestinal Tract*, pp. 301–322, Falk Symposium 62, (eds) Dowling et al., Academic Publishers). Thus, the desired effect of the enzyme inhibitors (i.e. inhibiting cell growth by polyamine pool depletion) is circumvented by one or both of these homeostatic responses.

Based on the observation that increases in the polyamine pools suppress ODC and SAMDC activities, an alternative approach has been devised (Porter and Bergeron, 1988, in *Advances in Enzyme Regulation*, pp. 57–79, Pergamon Press). It proposes to identify polyamine analogs which behave like the natural polyamines in down-regulating ODC and SAMDC, but which lack the ability to perform in functions required for cell growth. $N^1,N^{12}$-bis(ethyl)spermine (BESPM), a N-bis(ethyl) analog of spermine, has served as a model compound for this strategy. A comparison of the chemical structures of spermine and BESPM is shown in FIG. 1. BESPM was found by in-vitro studies to rapidly suppress ODC and SAMDC, deplete natural polyamine pools, and inhibit cell growth at 1–10 uM (Porter et al., 1987, *Cancer Res.* 47:2821–2825). In addition, BESPM suppresses polyamine uptake (Byers and Pegg, 1990, *J. Physiol.* 142:460–467; and Kramer et al., 1993, *J. Cell. Physiol.* 115:399–407), and thus minimizes the ability of tumor cells to meet their polyamine requirement by taking them up from their environment. The potential for polyamine analogs as effective chemotherapeutic agents is evidenced by potent antitumor activity against several melanoma cell lines in-vitro (Porter et al., 1991, *Cancer Res.*, 51:3715–3720; Shappell et al., 1992, *Anticancer Res.*, 12:1083–1090) and correspondingly, in-vivo against MALME-3 and PANUT human melanoma tumors growing as xenografts in athymic mice treated with bis-ethyl spermine analogs (Bernacki et al., 1992, *Cancer Res.*, 52:2424–2430; Porter et al., 1993, *Cancer Res.* 53:581–586). Potent antitumor activity of bis-ethyl spermine analogs has also been demonstrated for pancreatic cancer cell lines in-vitro (Chang et al., 1992, *Cancer Chemother. Pharmacol.* 30:183–188) and correspondingly in-vivo against mouse xenografts of human pancreatic ductal adenocarcinoma cells (Chang et al., 1992, *Cancer Chemother. Pharmacol.* 30:179–182). The bis-ethyl spermine analog with the most potent antitumor efficacy, $N^1,N^{11}$-bis(ethyl)norspermine (BENSPM, also known as DENSPM) is the subject matter of a new drug application submitted to the FDA for approval of clinical trials at 3 research institutions.

Additional in-vitro studies show that BESPM, and related analogs also cause an profoundly large induction of the polyamine metabolizing enzyme spermidine/spermine $N^1$-acetyltransferase (SSAT) in certain human carcinoma cell lines. The following is a list of relevant prior art along with a brief description of each:

Libby et al. (*Arch. Biochem. Biophys.* 284: 238–244, 1991) and Casero et al. (*Biochem. J.*, 270: 615–620) describe isolation and partial characterization of human SSAT protein from BESPM-treated cell lines. Casero et al. report that the cytotoxic response of the NCI H157 human large cell lung carcinoma cell line to exposure to BESPM was associated with a high induction of SSAT in-vitro.

Porter et al. (1991, *Cancer Res.*, 51:3715–3720) describe the extreme induction of SSAT levels after treatment of human melanoma cell lines (MALME-3) in-vitro with BESPM and an even higher degree of induction with other bis-ethyl spermine analogs. Between two melanoma cell lines (LOX and MALME-3), which differentially induce SSAT activity, a correlation was established between enzyme induction and in-vitro growth sensitivity to the bis-ethyl spermine analogs.

Each of the above cited references discloses a high induction in the levels of SSAT after treatment of specific human solid tumor cell lines in-vitro with bis-ethyl spermine analogs. However, there is a need to establish a correlation between SSAT levels and tumor growth responses in animals. At the time of the invention, none of the references demonstrated the induction of SSAT levels following treatment of malignant solid tumor-bearing animals, i.e. in-vivo, nor did the references disclose correlation of malignant solid tumor growth sensitivity to bis-ethyl spermine analogs with induced SSAT levels in-vivo.

It is not known if the high induction of SSAT would occur in-vivo because of uncertainties related to the stability of SSAT-specific m-RNA intracellularly and the stability of the enzyme itself. Because the analogs may cause other cellular events in in-vitro systems (i.e. suppression of ODC/ SAMDC, depletion of polyamine pools, and possibly other DNA-related effects), it is important to demonstrate that SSAT induction in-vivo is prominent among those events and that it may be causally related to or indicative of antitumor activity. Because an event occurs in-vitro does not necessarily mean that the event occurs in-vivo. For instance, suppression of ODC and SAMDC is well recognized as an in-vitro effect of bis-ethyl spermine analogs. However, recent studies (Porter et al., 1993, *Cancer Res.* 53:581–586; Porter and Bergeron, 1988, supra) show that this effect does not occur in-vivo.

Moreover, it must be demonstrated that SSAT induction in-vivo occurs selectively, or to a greater degree in malignant solid tumor tissue relative to various normal tissues. Its potential usefulness as a tumor marker, and as a determinant of drug action, is highly dependent upon quantitatively selective induction of enzyme levels in tumor cells. At the time of the invention, the prior art discloses induction of enzyme in certain solid tumor cell lines in-vitro, but does not disclose relative enzyme levels in related normal tissue in-vivo.

Therefore, there exists a need for a sensitive biological response indicator for use in monitoring the clinical effectiveness of polyamine analog anticancer agents, including the bis-ethyl spermine analogs, which have potent anticancer activity against certain cancers comprising malignant solid tumors such as human melanoma, and human pancreatic adenocarcinoma, and which also induce SSAT activity. In addition, a method for evaluating therapeutic effectiveness of treatment, and for the sensitivity to treatment of an individual's tumor with analogs, such as a bis-ethyl spermine analog, is desired. Such methods will greatly facilitate the identification of, and chemotherapeutic treatment of individuals bearing malignant solid tumors sensitive to analogs that effect induction of SSAT such as bis-ethyl spermine analogs.

SUMMARY OF THE INVENTION

A primary object of the invention is to provide a method for evaluating the responsiveness of an individual's malignant solid tumor to treatment with polyamine analogs that effect SSAT induction such as bis-ethyl spermine analogs.

Another object of the invention is to provide a method for monitoring the therapeutic effectiveness of treatment, using this class of polyamine analogs, of an individual bearing malignant solid tumors sensitive to this class of analogs.

A further object of the present invention is to provide a method for determining a therapeutic regimen and treatment schedule for individuals undergoing chemotherapy with polyamine analogs that effect induction of SSAT.

In summary, the above is accomplished by providing a method wherein the levels of SSAT are measured in an individual's malignant solid tumor cells which have been previously exposed to treatment with a polyamine analog. Induction of SSAT may be used as indica of sensitivity to, therapeutic effectiveness of, and to determine clinically efficacious amounts of, polyamine analogs.

BRIEF DESCRIPTION OF THE DRAWINGS

A more complete appreciation of the invention, and its many attendant advantages thereof, and a better understanding of its features may follow by referring to the detailed description in connection with the accompanying figures, wherein:

FIG. 1 is a diagram depicting the chemical relationship between spermine and a polyamine analog comprising the bis-ethyl spermine analog $N^1,N^{1,2}$-Bis(ethyl) spermine.

FIG. 2 are diagrams depicting the chemical relationship between three selected bis-ethyl spermine analogs which differentially induce SSAT.

FIG. 3 is a bar graph depicting the in-vivo induction of SSAT activity following bis-ethyl spermine analog treatment.

FIG. 7 are diagrams depicting the pathways involving polyamines, and the effects of bis-ethyl spermine analogs on these pathways. Abbreviations used: AdoMet- S-adenosylmethionine; ADC- S-adenosyl -methionine decarboxylase (also known as dcAdoMet or SAMDC); MTA-5'methylthioadenosine; ODC- ornithine decarboxylase; PAO- polyamine oxidase; SSAT- spermidine/spermine-$N^1$-acetyl transferase; AcCoA- Acetyl CoA.

FIG. 7A is a flow chart depicting polyamine synthesis and back-conversion.

DETAILED DESCRIPTION

The method of using the induction of spermidine/spermine $N^1$-acetyltransferase as a prognostic marker or as a tumor response marker, in relation to treatment of malignant solid tumors with polyamine analogs, includes the direct measurement of SSAT activity in tumor biopsies, and also includes measurement of other determinants relating to SSAT levels such as detection of metabolic products of SSAT as found in tissue or serum; detection in tissue of amplified SSAT-specific messenger RNA (m-RNA) transcripts, measurements of corresponding changes in levels of enzymes affected by the induction of SSAT activity, and detection and quantification in tissue of increased amounts of the enzyme protein itself such as by enzyme-linked immunosorbent assay (ELISA).

Figure 2A:
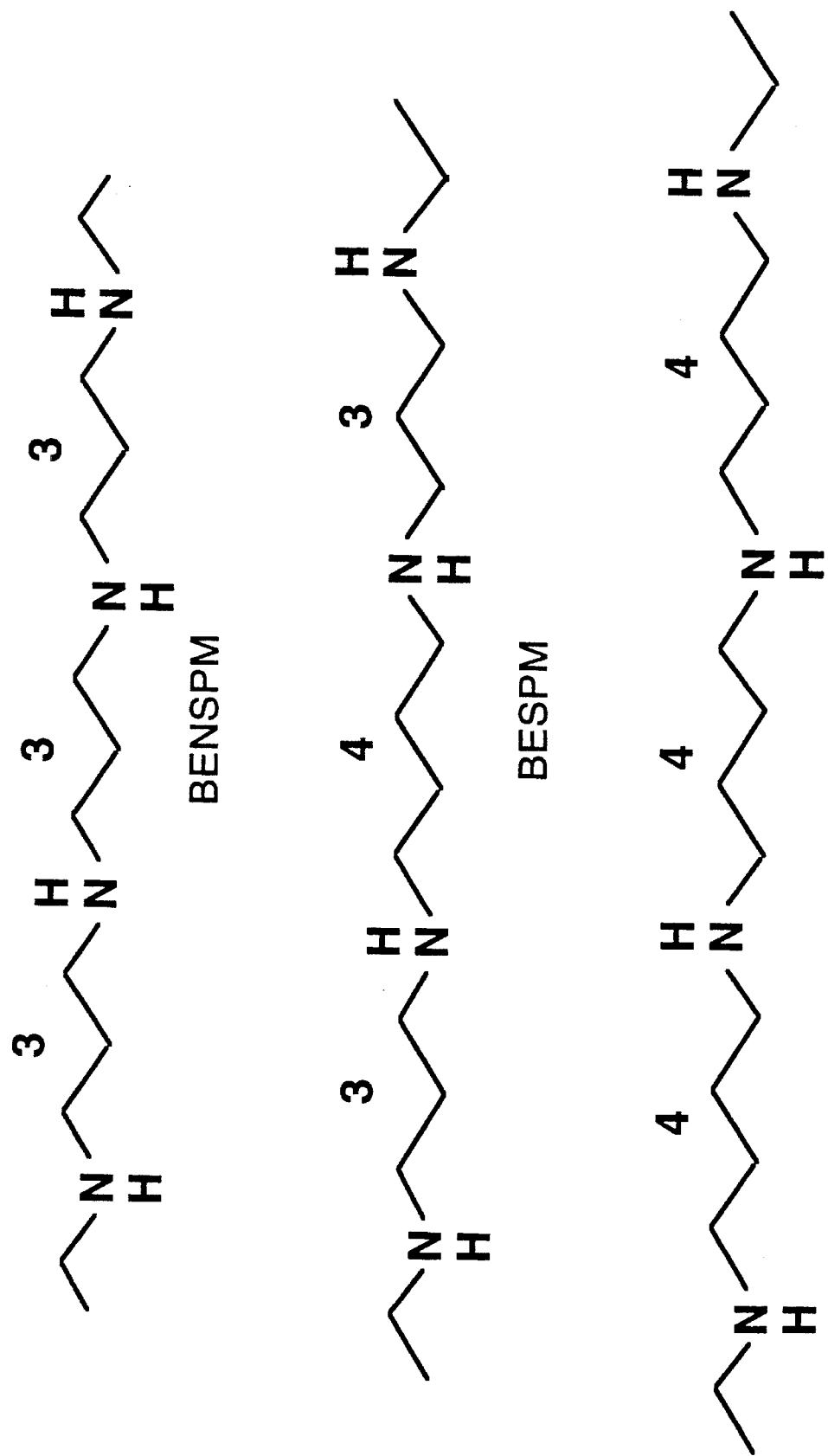
FIG. 2A is a diagram depicting the chemical relationship between three representative bis-ethyl spermine analogs.
Figure 2B:
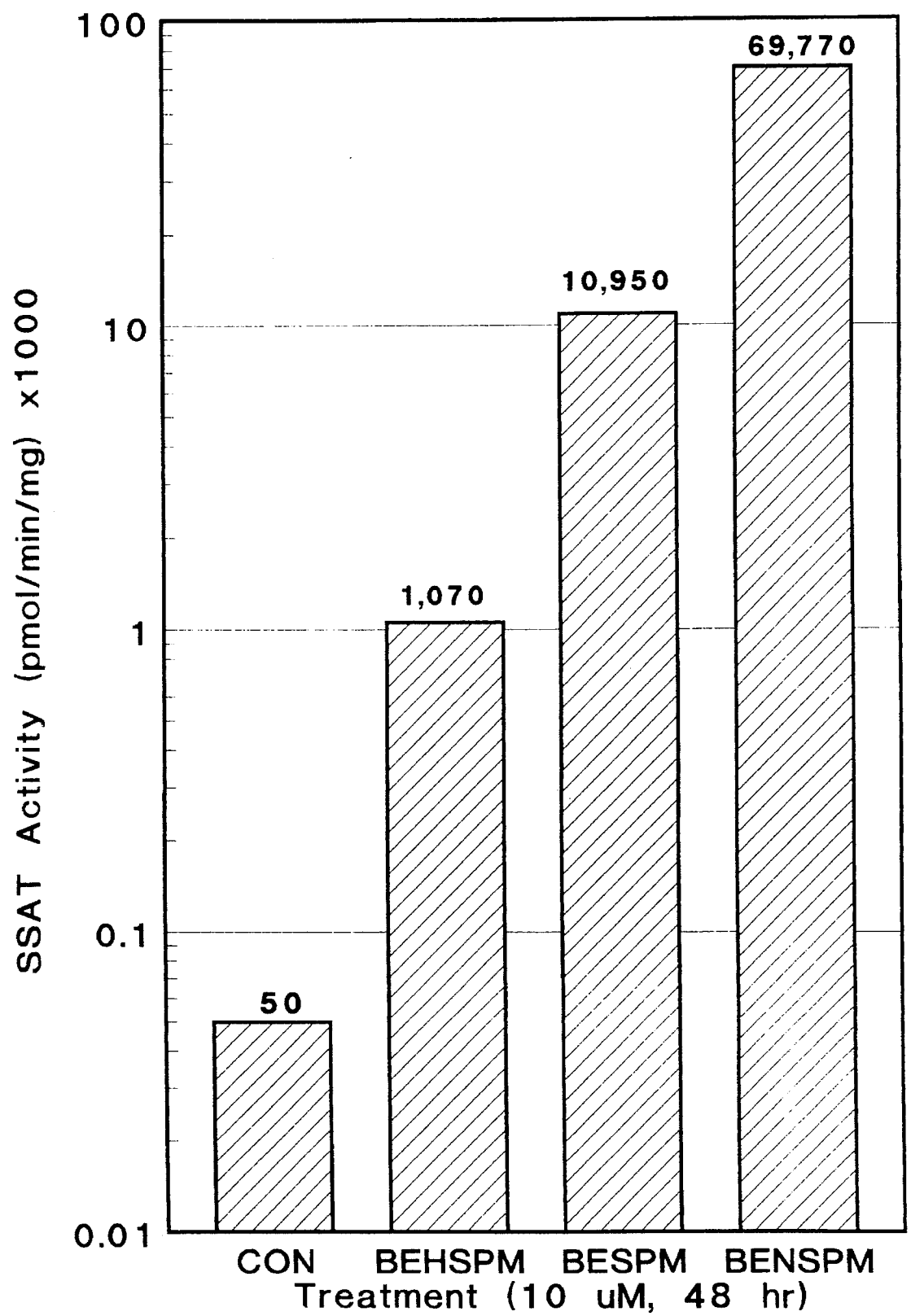
FIG. 2B is a bar graph depicting the relative abilities of the three bis-ethyl spermine analogs depicted in FIG. 2A to induce SSAT in MALME-3 human melanoma cells growing in culture. (Note that enzyme activity is expressed on a logarithmic scale).

The three bis-ethyl spermine analogs, chosen as a representative panel of polyamine analogs for use to perform relevant in-vivo studies, include $N^1,N^{12}$-bis (ethyl) spermine (BESPM); $N^1,N^{11}$-bis-(ethyl)norspermine (BENSPM) and $N^1,N^{14}$-bis(ethyl)homospermine (BEHSPM). All three similarly suppress ornithine and S-adenosyl-methionine decarboxylase levels, but differentially induce SSAT levels in-vitro (Porter et al., 1991, *Cancer Res.* 51:3715–3720, 1991; FIG. 2A). The chemical relationship between BESPM and the two related compounds, BEHSPM and BENSPM, is shown in FIG. 2B.

In the following embodiments used to illustrate the invention, it is important to consider the following concepts.

a. The use of athymic nude mice with human tumor xenografts has been validated as a model for the evaluation of chemotherapeutic agents because the model has been shown to reflect the clinical effectiveness of chemotherapeutic agents in original patients treated with these agents; and reflects antitumor effects from the agents, such as tumor regression or inhibition of tumor growth, as consistent with the activity against the corresponding types of clinical cancer (See for example, Neuwalt et al., 1985, *Cancer Res.* 45:2827–2833; Ovejera et al., 1978, *Annals of Clin.* and *Lab. Science* 8:50).

b. Anticancer effects of polyamine analog therapy are determined by assessing the antiproliferative activity on the treated solid tumor by measuring one or more responses including tumor growth suppression, tumor regression, or repression of regrowth. Tumors were measured in three dimensions and tumor volume was calculated according to the formula:

Volume=½(4π/3)(1/2)(w/2)(h)=0.5361 wh where 1 represents length; w—width; and h—height. Tumor sizes were monitored 2 times/week until the median volume ($V=0.4(a^2 \times b)$ where a is the smaller of the two perpendicular tumor diameters). As an indication of drug toxicity, animal weights were also recorded at the time of tumor volume measurement. Statistical analyses were performed on mouse tumor size and weight parameters by using the Mann-Whitney test.

Tumor growth suppression was measured by plotting the mean tumor volume versus the number of days post-inoculation with polyamine analog (growth curve analyses). Suppression is determined by comparison with the growth of untreated tumors (%T/C). More specifically,: %T/C is (treated tumor volume minus pretreatment volume) divided by (control tumor volume minus pretreatment volume)×100. Typically this is measured either when the control tumor volume reaches 1000 mm$^3$, or at the last day of treatment.

Tumor regression is measured as a percentage representing the average percentage of decrease in tumor volume from the largest pretreatment volume value.

Repression of regrowth is represented as regrowth delay, determined as the number of days following cessation of treatment when median group tumor volume exceeds 200 mm$^3$ (an arbitrary indication of regrowth which was determined statistically).

c. As will be apparent from the in-vivo studies described herein, and correlating with the in-vitro studies cited previously, cells from malignant, solid tumors of different origins respond to polyamine analogs heterotypically. SSAT induction and antitumor response will vary not only among the solid tumor tissue type, but also with the clonal line of malignant tumor of a particular solid tissue type. Such individual properties as the rate of growth of a particular solid tumor, and variations in the gene encoding SSAT, may affect its response to the polyamine analog. However, the heterotypic response should not be confused with the correlation between SSAT induction in-vivo and in-vitro with antitumor response in-vivo. In most malignant solid tumor types tested, those that exhibited induced SSAT levels after polyamine analog treatment in-vitro also exhibited a relative similar pattern of SSAT induction after treatment in-vivo; no tumor type tested showed a significant induction of SSAT in-vivo (levels of activity at least 10-fold over the control comprising either untreated tumor or untreated tissue of that particular origin) after polyamine analog treatment without also showing some measurable antitumor response in-vivo; and no tumor type tested showed a measurable antitumor response in-vivo after polyamine analog treatment without also showing significant induction of SSAT in-vivo. Further, consistent with the correlation is that when three polyamine analogs, which differentially induce SSAT levels in-vitro and in-vivo, were compared their ability to induce SSAT levels in-vitro corresponded to the relative ability of the analogs to induce SSAT levels in-vivo, and further corresponded to the potency of the antitumor effect in-vivo (Bernacki et al., 1992, supra). For example, when compared to two other bis-ethyl spermine analogs, BENSPM showed the greatest induction of SSAT in cells treated in-vitro and in cells treated in-vivo, and the most potent antitumor activity in cells treated in-vivo.

Correlation between Polyamine analog Induction of SSAT in-vitro and Induction of SSAT in-vivo To illustrate this embodiment, three polyamine analogs comprising bis-ethyl spermine analogs were used to treat MALME-3 human melanoma cells cultured in-vitro, and MALME-3 cells implanted as human xenografts in the athymic nude mouse model (Bernacki et al., 1992, supra). For in-vitro treatment, MALME-3 cells were maintained as a monolayer culture growing in RPMI 1640 containing 2% N-2-hydroxy-piperazine-N$^1$-ethanesulfonic acid/3-N-morpholinopropanesulfonic acid pH 7.4 as a buffer, 1 mM aminoguanidine as an inhibitor of serum oxidase, and 10% of a semidefined serum substitute. Cells were seeded at $2 \times 10^5$ cells/T-75 flask and incubated 24 hours before treatment with analogues. Following treatment with 10 μM of the respective bis-ethyl spermine analog, control and treated cultured cells were trypsinized, washed, and suspended for enzyme assays and cell number determinations. Control melanoma cells displayed a basal SSAT activity of approximately 50 pmol/min/mg. As illustrated in Table 1, the bis-ethyl spermine analogs differentially induced SSAT levels in-vitro, with the rank order of effectiveness in inducing SSAT levels being: BENSPM> BESPM> BEHSPM. As indicated in Table 1, the level of SSAT induction in-vitro by BESPM was about 10 fold that of BEHSPM, and the level of SSAT induction in-vitro by BENSPM was about 5 to 6 fold greater than that of BESPM.

For the in-vivo treatment, 10$^7$ cultured MALME-3 melanoma cells were injected subcutaneously into 20 gram female nude athymic mice. After four in-vivo passages, tumor was removed and 40–50 mm$^3$ fragments were selected for implantation into mice via subcutaneous trocar implantation. Mice developing palpable tumors of a similar size were divided into different treatment groups comprising mice per group. Following treatment of the mice with a dosage approaching the maximally tolerated dose of the respective bis-ethyl spermine analog, the tumor cells comprising the human xenograft were removed and assayed for SSAT induction. The control melanoma cells cultured in-vivo displayed a basal SSAT activity of approximately 75 pmol/min/mg. As illustrated in Table 1, the bis-ethyl spermine analogs differentially induced SSAT levels in-vivo, with the rank order of effectiveness in inducing SSAT levels being: BENSPM> BESPM> BEHSPM. Also indicated in Table 1, the level of SSAT induction in-vivo by BESPM was less than 20 fold that of BEHSPM, and the level of SSAT induction in-vivo by BENSPM was about 6 fold greater than that of BESPM. Thus, a conclusion from the results depicted in Table 1 is the rank order in effectiveness of the bis-ethyl spermine analogs to induce SSAT levels in-vitro correlated well with their effectiveness to induce SSAT levels in-vivo.

TABLE 1

Correlation of Induction of SSAT In-vitro and In-vivo

| Homolog | SSAT Induction | |
|---|---|---|
| | In-vitro (pmol/min/$10^6$ cells) | In-vivo (pmol/min/mg) |
| Control | 51 | 75 |
| BEHSPM | 1108 | 125 |
| BESPM | 11,525 | 2,360 |
| BENSPM | 64,345 | 15,700 |

5 mice per treatment group, treated every 8 hours for 6 days. 10 mice per control group.

In accordance with the above methods for assaying the induction of SSAT levels in tumor cell lines treated in-vitro and xenografts treated in-vivo, the induction pattern also correlates fairly well amongst different clonal lines of a particular tumor type. This can be illustrated with melanoma clonal lines LOX, SH-1, PANUT-3, and MALME-3. Table 2 shows the level of SSAT induction of these clonal lines treated in-vitro with 10 μm BESPM, and the level of SSAT induction (16 hours post-treatment) of these clonal lines treated in-vivo with BENSPM (40 mg/kg, 3 times per day, for 6 days).

TABLE 2

SSAT Induction in Melanoma Clonal Lines

| Clonal Line | SSAT Induction | |
|---|---|---|
| | In-vitro (pmol/min/$10^6$ cells) | In-vivo (pmol/min/mg) |
| LOX | 171 | 160 (200/115) |
| SH-1 | 1100 | 7,150 (7,495/6,810) |
| PANUT-3 | 10,343 | 25,575 (23,140/22,010) |
| MALME-3 | 19,520 | 13,710 (11,490/15,930) | control SSAT induction for each clonal line tested in-vivo ranged between 40–90 pmol/min/mg.

Although SSAT levels induced in-vitro in PANUT-3 following BESPM treatment were less than those in MALME-3 cells similarly treated, further studies of treatment of PANUT-3 and MALME-3 with BENSPM in-vitro showed that in fact SSAT levels were induced to greater levels in PANUT-3 than in MALME-3 (Porter et al., 1993, Cancer Research 53:581–586) correlating with BENSPM induction in-vivo.

In accordance with the above methods for assaying the induction of SSAT levels in tumor cell lines treated in-vitro and xenografts treated in-vivo, the induction pattern also correlates fairly well amongst carcinomas of solid organs. This can be illustrated with malignant clonal lines A121, A549, and HT29. Table 3 shows the level of SSAT induction of these clonal lines treated in-vitro with 10 μm BENSPM, and the level of SSAT induction (16 hours post-treatment) of these clonal lines treated in-vivo with BENSPM (40 mg/kg, 3 times per day, for 6 days).

TABLE 3

Induction in Carcinoma Clonal Lines

| Clonal Line, tissue type | SSAT Induction | |
|---|---|---|
| | In-vitro (pmol/min/$10^6$ cells) | In-vivo (pmol/min/mg) |
| A121, ovarian | 2,700 | 2,905 (3,180/2,630) |
| A549, lung | 22,755 | 14,295 |
| HT29, colon | 3,640 | 3,535 (2,895/4,175) |

SSAT Induction in-vivo, and Correlation of in-vivo Antitumor Activity of N,N'-Bis(ethyl)spermine Analogs with SSAT Induction A. Comparison of the rank order of analogs in effectiveness of inducing SSAT levels in-vitro and in-vivo with the rank order of the analogs in potency of antitumor response.

The in-vivo antitumor activities of BESPM, BEHSPM, and BENSPM, were compared against various human xenografts in nude athymic mice. Cultured human tumor cells were first passaged several times in female HSD nude athymic mice. Fragments of resultant tumor were implanted into mice via subcutaneous trocar implantation. Mice of different treatment groups were treated with one or more of the three bis-ethyl spermine analogs BESPM, BEHSPM, and BENSPM. Anti-proliferative activity was monitored by antitumor responses including tumor growth suppression, tumor regression, or repression of regrowth.

As illustrated in Table 1 with MALME-3 human melanoma cells, the rank order effectiveness of three polyamine analogs in inducing SSAT levels both in-vitro and in-vivo were BENSPM> BESPM> BEHSPM, with substantial differences in induction between them. The same three polyamine analogs were analyzed for their effectiveness in inducing a potent antitumor response in-vivo. Mice developing palpable tumors of a similar size were divided into different treatment groups comprising 5 mice per treatment group, and 10 control mice per treatment group. The treatment groups, and treatment regimen. per group, were as follows: BEHSPM: administered every 8 hours for a 6 day period with group 1 receiving 1.5 mg/kg; group 2 receiving 3.0 mg/kg; and group 3 receiving 6.0 mg/kg.

BESPM: administered every 8 hours for a 6 day period with group 1 receiving 10 mg/kg; group 2 receiving 20 mg/kg; and group 3 receiving 40 mg/kg.

BENSPM: administered every 8 hours for a 6 day period with group 1 receiving 20 mg/kg; group 2 receiving 40 mg/kg; and group 3 receiving 80 mg/kg.

Note that the highest drug dosages for each analog approach the maximally tolerated dosage for that particular analog (for example, BEHSPM at 6 mg/kg; BESPM at 20 mg/kg; and BENSPN at 80 mg/kg were tolerated by treated animals, whereas higher doses were toxic). Tumor cells comprising the human xenograft were removed from two animals of each group and assayed for SSAT induction. The melanoma cells for each control group displayed a basal SSAT activity of between 50–100 pmol/min/mg. Table 4 illustrates the dose for each polyamine analog which resulted in the most significant antitumor response. As shown in Table 4, against the MALME-3 human melanoma xenografts in mice, BESPM displayed significant antitumor activity evidenced by the suppression of tumor growth for an additional 30 days following cessation of treatment. By comparison, BEHSPM was less effective than BESPM, in that BEHSPM suppressed tumor growth for 18 days after cessation of treatment. BENSPM was the most effective of the three in that it suppressed tumor growth for 40 days after the cessation of treatment. Thus, the antitumor activity for these three analogs correlated with their ability to induce SSAT activity in the same tumor cells growing in-vitro and in-vivo, with the rank order of effectiveness in inducing SSAT levels being: BENSPM> BESPM> BEHSPM (Table 4).

TABLE 4

Correlation of Polyamine Analog Induction of SSAT with Antitumor Response In-vivo

| Polyamine analog | SSAT Activity | | Antitumor Response | |
|---|---|---|---|---|
| | In-vitro[a] | In-vivo[b] | Regrowth Delay* | % T/C** |
| Control | 51 | 75 | 0 | 100 |
| BEHSPM | 1108 | 125 | 14 | 43 |
| BESPM | 11525 | 2360 | 27 | 34 |
| BENSPM | 64345 | 15700 | 37 | 10 |

[a]measured in pmol/min/$10^6$ cells after treatment with 10 μM of analog.
[b]measured in pmol/min/mg after treatment with maximally tolerated dose.
*Regrowth delay, explained above, is the time in days required following treatment for median tumor volume to reach 200 $mm^3$.
**% T/C is a measure of tumor growth suppression as explained previously.

It was also noted that retreatment 2 weeks later with BENSPM resulted in an apparent curing of about 20% of the MALME-3 xenografts. This antitumor activity exhibited is sufficiently significant to warrant clinical testing of polyamine analogs that effect SSAT induction, and in particular, BENSPM. It is also noteworthy that while the rank-order for analog induction of SSAT in-vitro and in-vivo agreed with the ranking for antitumor effect, the rank-order was opposite to the relative effect on host toxicity indicating that while SSAT induction may play a role in analog efficiency against tumors, it is not related to toxicity.

B. Comparison of induction of SSAT in normal tissue and tumor tissue following polyamine analog treatment in-vivo.

Additional studies were performed using BENSPM treatment of human xenografts to determine if there exists a correlation between antitumor activity and SSAT induction in-vivo. SSAT activity was measured using cell extracts obtained by sonication, in 5 mMN-2 hydroxypiperazine-$N^2$-ethanesulfonic acid (pH 7.2) containing 1 mM dithiothreitol, of tumor biopsy from treated mice, and tumor biopsy from control mice. The cytosolic extract resulting from a 1 hour centrifugation at 35,000 rpm in a Spinco 40 rotor was used as the source of the enzyme for the assay of SSAT activity. The cytosolic extract was incubated with 10 μmol HEPES buffer, pH7.8, 0.15 nmol spermidine, and 0.5 nmol [1-$^{14}$C] acetylCoenzyme A, in a final volume of 50 μl, for 5 minutes at 37° C. The reaction was stopped by chilling, the addition of 20 μl of 0.5 M $NH_2OH.Cl$, and heating in a boiling water bath for 3 minutes. After centrifugation to remove precipitated protein, 50 μl of the reaction was spotted on a disc of P-81 phosphocellulose and counted for radioactivity. Protein concentration was also measured so that enzyme activity was expressed as picomoles of acetylspermine synthesized per minute per milligram of protein.

To illustrate this embodiment, SSAT activity was analyzed in tumor tissue and normal tissue from 2 mice following BENSPM treatment of 5 mice at 40 mg/kg, three times daily, for 6 days (Porter et al., 1993, supra). The purpose of this analysis was to examine the difference in tissue responsiveness to SSAT induction in-vivo between tumor tissue and normal tissue wherein the BENSPM tissue content was similar for both tumor and normal tissues. SSAT in MALME-3 tumors taken 16 hours following the final BENSPM injection, was elevated to approximately 13,700 pmol/min/mg as compared with the activity of 75 pmol/min/mg in control tumors (Table 5). Also kidney and liver SSAT activities in the mice treated with BENSPM were found to be increased from basal levels of approximately 10 pmol/min/mg to 1255 and 320 pmol/min/mg, respectively. BENSPM-treated tumors had polyamine pools which were almost totally depleted at this time. Two weeks after treatment, the tumor from MALME-3 human melanoma xenografts in BENSPM-treated mice contained SSAT levels of 3,040 pmol/min/mg as compared to 260 and 75 pmol/min/mg for kidney and liver, respectively. Note that ODC and SAMDC levels were not suppressed, suggesting that polyamine depletion may be due totally to SSAT induction. Thus, the latter may be indirectly responsible for growth inhibition and, therefore, a determinant of drug action in-vivo. This embodiment further illustrates the high inducibility of SSAT in these human melanoma lines, which has been observed in-vitro (Tables 1 & 2, supra; Porter et al., 1991, supra; and Shappell et al., 1992, supra), also occurs in-vivo.

TABLE 5

Effect of BENSPM on MALME-3 Melanoma and Host Tissue Polyamine-Related Enzymes

| | | Enzyme Activities | | |
|---|---|---|---|---|
| Tissue | BENSPM Treated* | QDC (nmol/hr/mg) | SAMDC (nmol/hr/mg) | SSAT (pmol/min/mg) |
| 16 Hrs Post-treatment: | | | | |
| Tumor | − | 0.23/0.13** | 0.35/0.28 | 67/83 |
| | + | 0.21/0.16 | 0.42/0.41 | 11,490/15,930 |
| Kidney | − | 0.16/0.14 | 0.25/0.36 | 6/8 |
| | + | 0.18/0.21 | 0.56/0.47 | 1616/895 |
| Liver | − | 0.11/0.08 | 1.05/1.68 | 11/8 |
| | + | 0.21/0.15 | 1.23/1.03 | 347/294 |
| 2 Wks Post-treatment: | | | | |
| Tumor | − | 0.17/0.20 | 0.62/0.65 | 70/75 |
| | + | 0.28/0.99 | 0.96/2.14 | 2810/3275 |
| Kidney | − | 0.14/0.13 | 0.26/0.33 | 5/3 |
| | + | 0.13/0.13 | 0.49/0.37 | 272/248 |
| Liver | − | 0.06/0.06 | 1.27/1.32 | 6/5 |
| | + | 0.06/0.08 | 1.01/1.14 | 90/60 |

**40 mg/kg 3x/day × 6 days
**Duplicate mice with each value representing the mean of duplicate assays.

Figure 4:
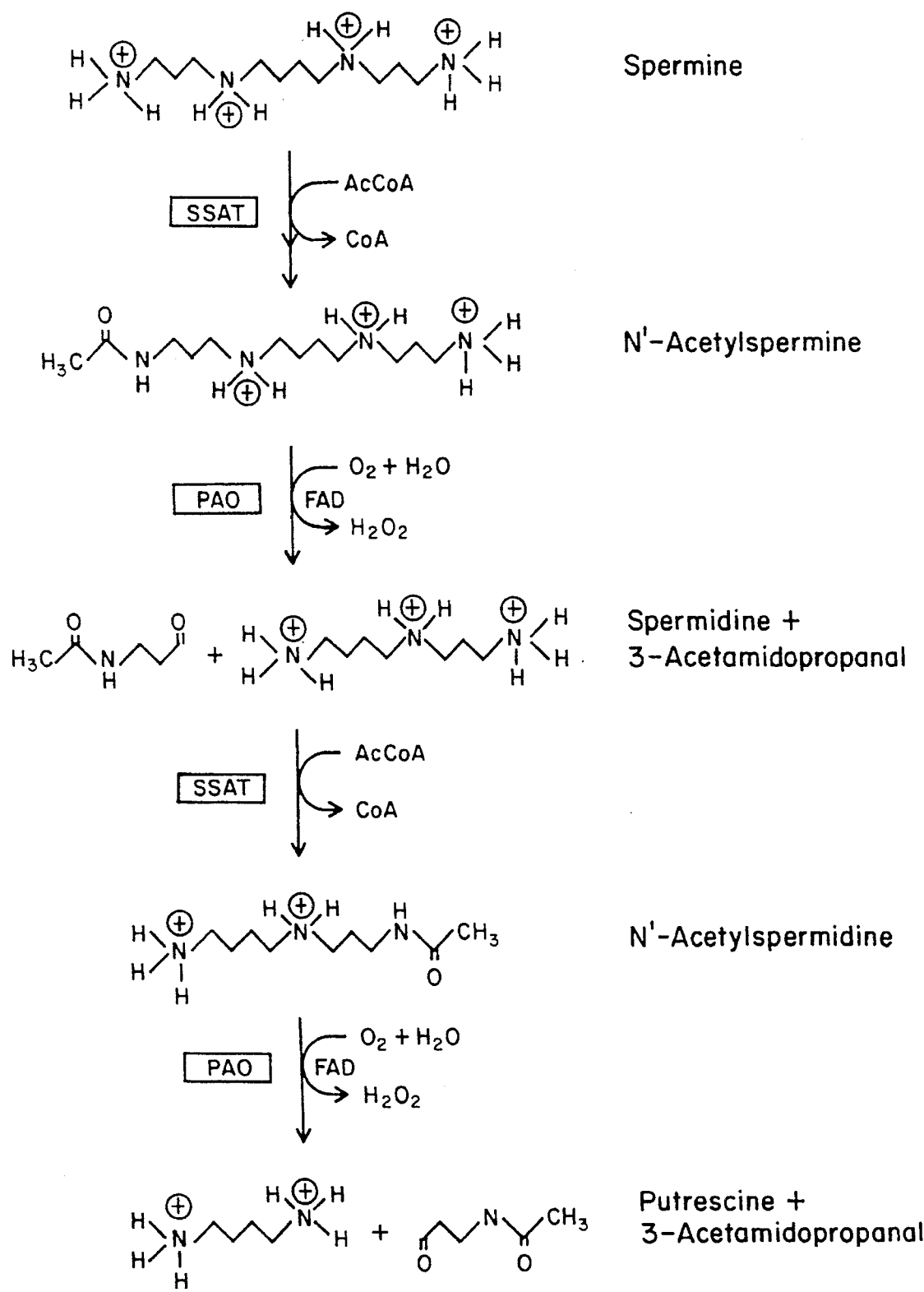
FIG. 4 is a diagram depicting a biochemical pathway involving spermine and derivatives thereof.

In another illustration of this embodiment, SSAT in PANUT-3 tumors taken 16 hours following the final BENSPM injection, was elevated to approximately 22,500 pmol/min/mg as compared with the activity of 55 pmol/min/mg in control tumors (Table 6). Also kidney and liver SSAT activities in the mice treated with BENSPM were found to be increased from basal level range of from 10–50 pmol/min/mg to induced levels of 1550 and 583 pmol/min/mg, respectively. BENSPM-treated tumors had polyamine pools which were almost totally depleted at this time. Two weeks after treatment, the tumor from PANUT-3 human melanoma xenografts in BENSPM-treated mice contained SSAT levels of 130 pmol/min/mg as compared to 58 and 13 pmol/min/mg for kidney and liver, respectively. Note that ODC and SAMDC levels were not suppressed. Note also that following BENSPM treatment, suppression of tumor growth of PANUT-3, unlike suppression of MALME-3 growth, lasted for only about 12 days. Thus, the levels of SSAT in PANUT-3 at two weeks post-treatment, approaching the levels in the control, correlate with the loss of antitumor activity. This illustration of the embodiment not only confirms the high inducibility of SSAT in these human melanoma lines, observed in-vitro (Table 2, supra; and Shappell et al., 1992, supra), also occurs in-vivo; but also shows a correlation between SSAT induction in-vivo and antitumor response in-vivo.

spermidine and spermine thus eliminating availability of free polyamines; an excessive accumulation of $N^1$-acetylspermidine; depletion of acetylCoenzyme-A pools (co-factor for SSAT as shown in FIG. 4); inappropriate acetylation of and possible inactivation of critical molecules or receptors; or any combination of the above.

TABLE 6

Effect of BENSPM on PANUT-3 Melanoma and Host Tissue Polyamine-Related Enzymes

| | | Enzyme Activities | | |
|---|---|---|---|---|
| Tissue | BENSPM Rx* | QDC (nmol/hr/mg) | SAMDC (nmol/hr/mg) | SSAT (pmol/min/mg) |
| 16 Hrs Post-treatment: | | | | |
| Kidney | − | 0.02/0.03** | 0.10/0.17 | 50/29 |
| | + | 0.54/0.58 | 0.42/0.40 | 626/1475 |
| Liver | − | 0.02/0.06 | 2.18/2.99 | 9/16 |
| | + | 0.21/0.24 | 2.50/1.13 | 816/350 |
| Spleen | − | 0.04/0.13 | 0.41/0.13 | 42/24 |
| | + | 0.20/0.04 | 0.28/0.37 | 163/322 |
| PANUT Tumor | − | 0.08/0.27 | 0.00/0.25 | 39/72 |
| | + | 0.72/0.02 | 0.06/0.08 | 23140/22012 |
| 2 Wks Post-treatment: | | | | |
| Kidney | − | 0.03/0.05 | 0.04/0.16 | 93/24 |
| | + | 0.03/0.03 | 0.15/0.12 | 56/60 |
| Liver | − | 0.01/0.04 | 2.14/2.71 | 13/10 |
| | + | 0.05/0.01 | 1.06/1.63 | 7/19 |
| Spleen | − | 0.01/0.02 | 0.42/0.34 | 68/46 |
| | + | 0.01/0.01 | 0.22/0.13 | 48/40 |
| PANUT Tumor | − | 0.12/0.08 | 0.23/0.15 | 158/12 |
| | + | 0.13/0.05 | 0.47/0.39 | 127/137 |

*80 mg/kg 3x/day × 6 days
**Enzyme levels for duplicate mice.

Regarding reproducibility of enzyme measurements in-vivo, it should be noted that there exists close agreement between SSAT enzyme activities for normal tissue per paired mice, and cells of malignant solid tumors per paired mice, from the same experiment as represented in Tables 2–7. In addition, normal tissue values presented in Tables 5, 6, and 7 derive from three separate experiments and are within the range of biological variation for an in-vivo system.

C. Mechanistic correlation of SSAT induction with antitumor activity.

In the absence of other major biochemical perturbations, the dramatically increased SSAT levels in treated tumor seem to suggest a role for the enzyme in the initiating growth inhibition during treatment and in sustaining the effect after treatment (FIG. 3).

Figure 7B:
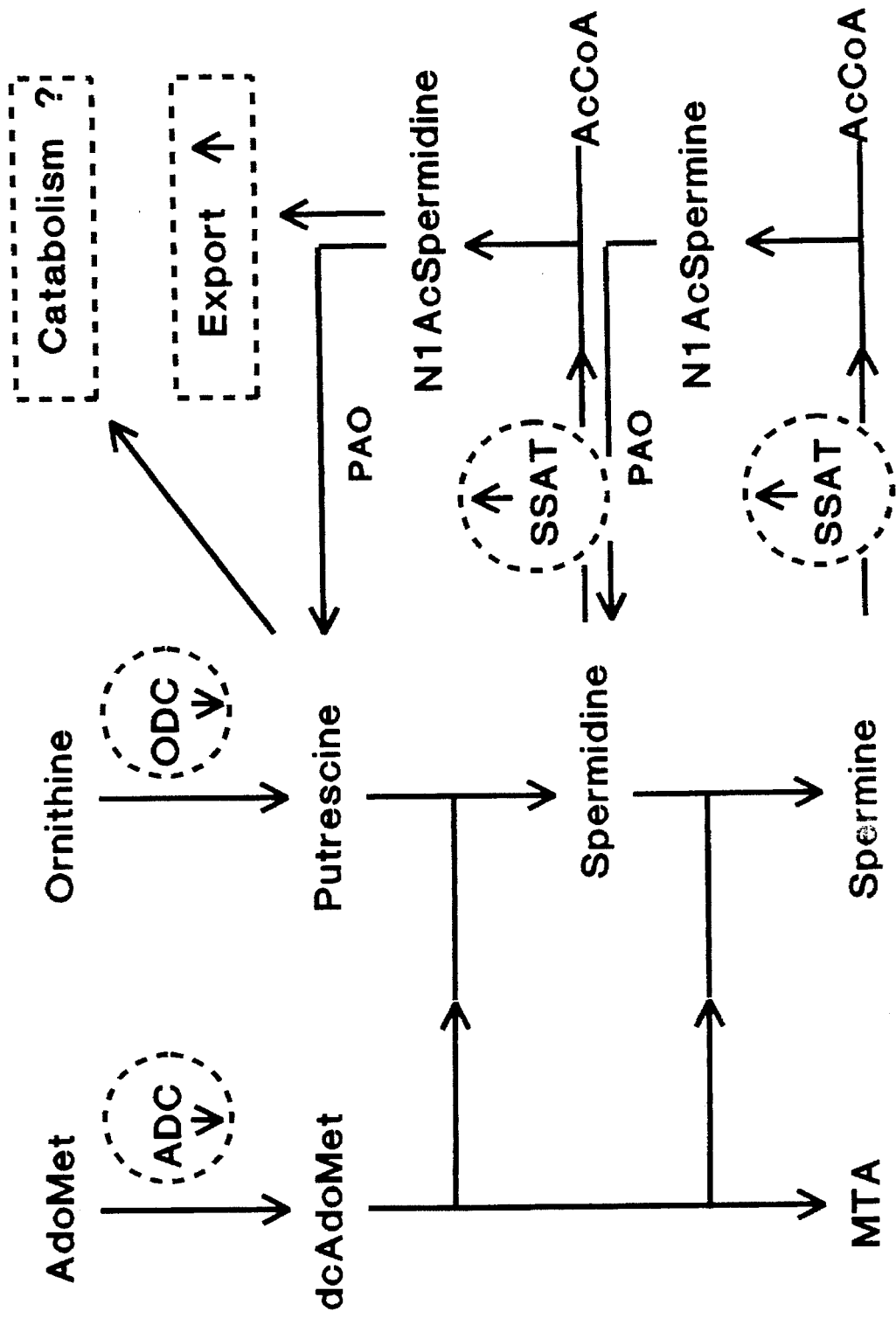
FIG. 7B is a flow chart showing the known in-vitro effects of bis-ethyl spermine analogs on the pathways depicted in FIG. 7A.

The level of polyamine depletion achieved in malignant solid tumors treated in-vivo with BENSPM (Table 7) is sufficient by in-vitro standards based on specific inhibitors of polyamine biosynthesis to inhibit cell growth (Porter et al. 1993, supra, Falk Symposium). Since this is accomplished in the absence of ODC and SAMDC suppression (as shown in Tables 5 and 6), polyamine catabolism and excretion due to SSAT induction (FIG. 7B) appears to be directly linked to antitumor activity and hence, a determinant of polyamine analog drug action.

Since polyamine pools at the two week period (Table 7) are not characteristic of polyamine inhibitor-induced growth inhibition (i.e. pools are not markedly depleted), SSAT may mediate the antiproliferative response by other means. These other means may include rapid acetylation of all unbound

TABLE 7

Effect of BENSPM on MALME-3 Melanoma and Host Tissue Polyamine and Analog Pools

| Tissue | BENSPM Treated* | PUT | SPD | SPM | BENSPM |
|---|---|---|---|---|---|
| | | | (pmol/mg protein) | | |
| 16 Hrs Post-treatment: | | | | | |
| Tumor | − | 60/20** | 320/290 | 450/380 | — |
| | + | 20/20 | 50/20 | 40/30 | 1020/1535[b] |
| Kidney | − | 20/20 | 240/260 | 540/440 | — |
| | + | 100/40 | 100/100 | 260/250 | 860/1705[b] |
| Liver | − | 20/20 | 570/460 | 610/500 | — |
| | + | 90/100 | 80/90 | 170/200 | 1180/1470[b] |
| 2 Wks Post-treatment: | | | | | |
| Tumor | − | 20/50 | 330/270 | 330/360 | — |
| | + | 370/290 | 560/160[a] | 200/80 | 620/470 |
| Kidney | − | 20/30 | 340/320 | 530/520 | — |
| | + | 20/20 | 210/210 | 360/370 | 90/150 |
| Liver | − | 20/20 | 490/660 | 660/760 | — |
| | + | 20/20 | 530/530 | 400/330 | 40/40 |

*BENSPM 40 mg/kg 3x/day × 6 days.
**Duplicate mice with each value representing the mean of duplicate determinations.
[a] Also contained high levels of N-acetylspermidine (240/180 pmol/mg protein).
[b] Also contained a peak which was similar in height to the SPM peak of this tissue and which was presumed by location to be a monoethyl metabolite peak of BENSPM.

D. SSAT induction versus tumor growth-a heterotypic response.

Figure 5:
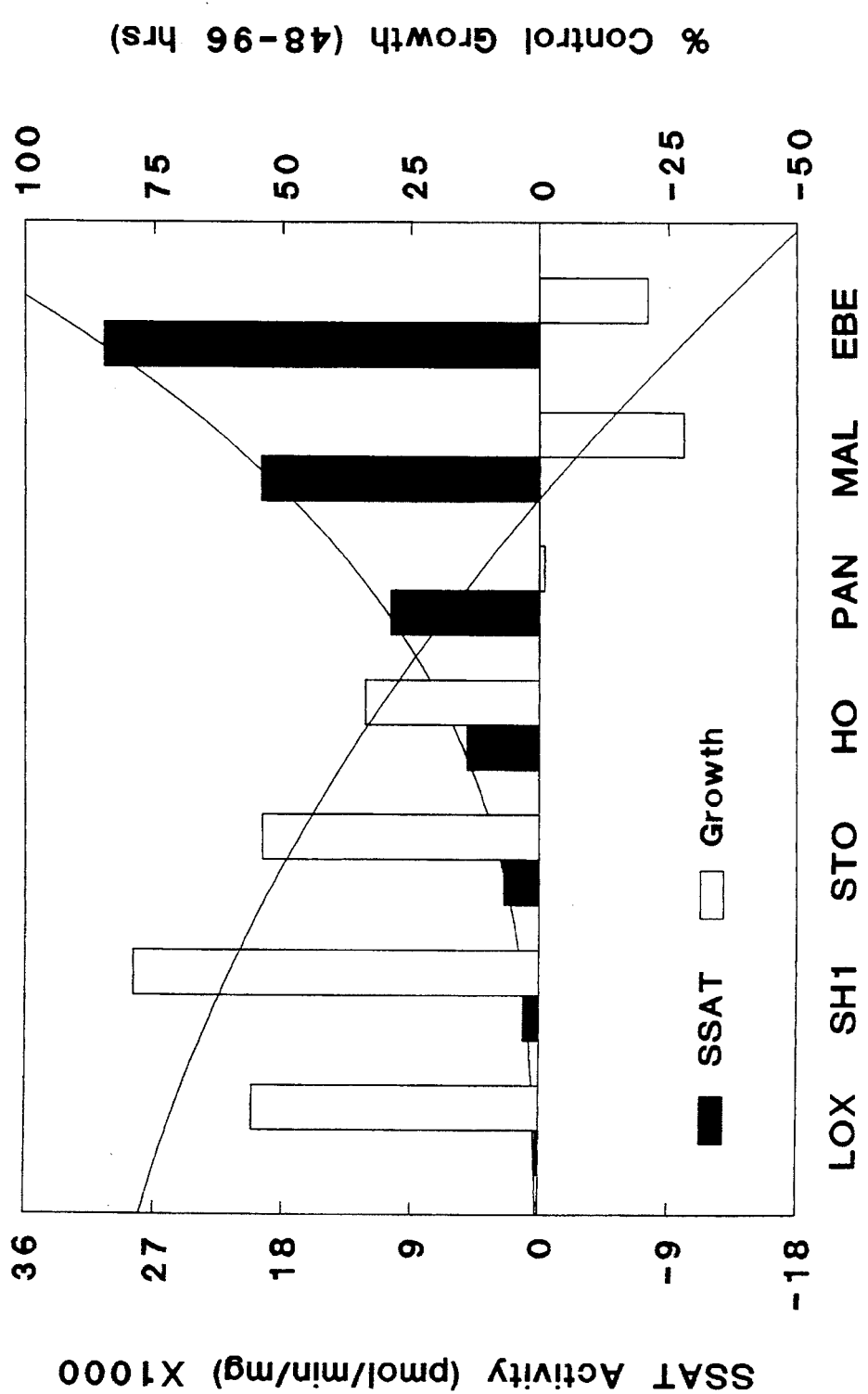
FIG. 5 is bar graph comparing SSAT induction with growth (as a measure of antitumor response) of several human melanoma cell lines treated in-vitro for 48 hours with 10 μm BESPM.

As mentioned previously, cells from malignant solid tumor respond to polyamine analog therapy heterotypically. SSAT induction and antitumor response may vary not only among the solid tumor tissue type, but also with the clonal line of tumor of a particular solid tissue type. However, a correlation between the level of induction of SSAT and the potency of antitumor response has been observed in tumors of a particular solid tissue type. For example, seven human melanoma cell lines were assayed in-vitro for their response, as determined by cell growth and level of SSAT induction, to 10 µM BESPM at 48 hours post-treatment. As summarized in FIG. 5, growth among the cell lines decreases as SSAT induction increases. Thus, human melanoma cell lines LOX and SH-1 showing the lowest induction of SSAT levels also were the cell lines to show the least growth inhibition. Similarly, human melanoma cell lines MALME-3 and Ebey showing the highest SSAT activity also displayed the greatest growth inhibition (negative growth indicates cytotoxicity).

Figure 6:
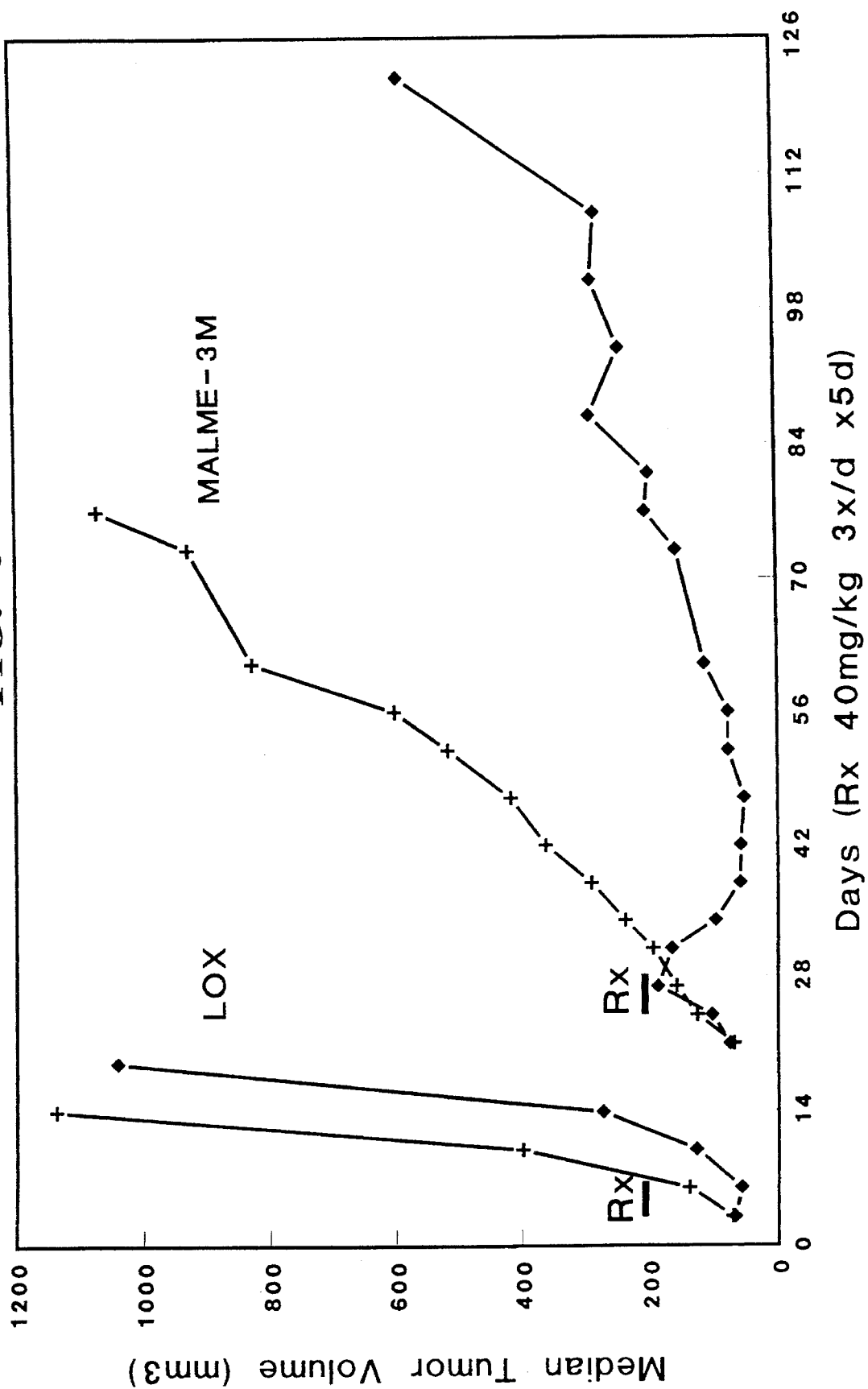
FIG. 6 is a graph showing SSAT activity vs. antitumor activity (as measured by median tumor volume) examined in LOX and MALME-3 melanoma human xenografts in untreated mice, and mice treated with polyamine analog.

This correlation between level of SSAT induction and potency of antitumor response can also be demonstrated in-vivo. For example, SSAT activity and potency of antitumor response was examined for LOX and MALME-3 melanoma xenografts in mice. Mice developing palpable tumors of a similar size were divided into different treatment groups comprising 7 mice per treatment group, and 7 control mice per treatment group. The treated mice received 40 mg/kg of BENSPM administered every 8 hours for a 5 day period. Melanoma tumor cells comprising the human xenografts were removed from two mice of each group at 16 hours following the final BENSPM injection to evaluate the level of induction of SSAT activity. The antitumor response from polyamine analog therapy was assessed in the five remaining mice from each group by monitoring the tumor volume of the xenografts over days following treatment as compared to untreated xenografts. The tumor cells for each control group displayed a basal SSAT activity of between 40–100 pmol/min/mg. Note that in viewing the antitumor effects caused by polyamine analog treatment of LOX versus MALME-3 xenografts, shown in FIG. 6, the level of induction of SSAT was 160 pmol/mg/min in LOX xenografts, whereas significantly more SSAT activity was induced by the polyamine analog in the MALME-3 xenografts (24,018 pmol/mg/min). As shown in FIG. 6 (+= control, ♦= treated), human xenografts comprising the LOX melanoma cell line showed no significant tumor regression, regrowth delay, nor lack of regrowth as compared to LOX xenografts from the control mice. However, as shown in FIG. 6 (+= control, ♦= treated), human xenografts comprising the melanoma cell line MALME-3 showed tumor regression; significant regrowth delay; and lack of regrowth was observed in two mice examined of the remaining five mice treated. Thus, human melanoma cell line (LOX) showing low or no induction of SSAT levels after polyamine analog treatment also showed the least antitumor response, as compared to human melanoma cell line (MALME-3) which showed a significant level of induction of SSAT activity as well as displaying a potent antitumor response.

Further evidence of the correlation between level of SSAT induction and potency of antitumor response in-vivo following polyamine analog treatment may be demonstrated among clonal lines of tumor of a particular solid tissue type. For example, human melanoma cell lines including MALME-3, SH-1, PANUT-3 and LOX were evaluated for the level of SSAT induction and potency of antitumor response following BENSPM treatment (80 mg/kg 3×/day×6 days) using the methodology previously described in this embodiment. Also, antitumor responses were compared using different doses of BENSPM (80 mg/kg versus 40 mg/kg), with the result being that the antitumor response at 40 mg/kg was very similar to the response at 80 mg/kg. The baseline of SSAT activity in the control mice (2 examined of 7 mice) ranged from 50 to 90 pmol/min/mg. As summarized in Table 8, the human melanoma clonal lines that demonstrate the highest induction of SSAT activity (MALME-3 and PANUT-3) also were the cell lines that demonstrated the most potent antitumor responses. In comparing the responses of MALME-3 and PANUT-3 following polyamine analog treatment in-vivo, SSAT activity is induced to a higher level in PANUT-3, and PANUT-3 cells demonstrate significantly more tumor regression after cessation of treatment. Note that following BENSPM treatment (as discussed above in the context of Tables 4 and 5), suppression of tumor growth of PANUT-3, unlike suppression of MALME-3 growth, lasted for only about 12 days. Further, the levels of SSAT in PANUT-3 at two weeks post-treatment, approached the levels in the control and correlated with the loss of antitumor activity. Thus, over the duration of this experiment, in measuring regrowth the levels of SSAT were still likely induced in MALME-3 cells but not in PANUT-3 cells. Thus, the observation that MALME-3 exhibits more of an antitumor response when the parameter of regrowth is examined, may reflect the differences in the extent to which elevated SSAT levels are retained after polyamine analog treatment.

TABLE 8

Summary Comparison of BENSPM-Induced SSAT and Antitumor Responses

| Tumor Line (human) | Doubling Time (dt) (days) | Avg. SSAT Activity** (pmol/min/mg) | Antitumor Responses*** (BENSPM at 80 mg/kg) | | | |
|---|---|---|---|---|---|---|
| | | | % T/C at 1 g | Tumor Regression | Regrowth Delay | No Regrowth+ |
| MALME-3M | 13 | 13,710 | <0* | Present | >4.8 × dt | 2/5 |
| SH-1 | 15 | 7,150 | <0 | Present | 2.1 × dt | 1/5 |
| PANUT-3 | 7 | 22,750 | 10 | Major | 2.7 × dt | 0/5 |
| LOX | 5 | 157 | 40 | None | None | 0/5 |

*After cessation of treatment [times tumor doubling time (dt)]
**Measured 24 hours after final treatment
***Based on median values of at least 5 mice per group
+For duration of experiment Cells from malignant solid human tumor tissue types, other than melanoma, have also been evaluated for their responsiveness to polyamine analog treatment including clonal cell lines A121 (human ovarian adenocarcinoma), A549 (lung adenocarcinoma), and HT29 colon adenocarcinoma). These cell lines were evaluated for the level of SSAT induction and potency of antitumor response following BENSPM treatment (80 mg/kg 3×/day×6 days) in-vivo using the methodology previously described in this embodiment. Also, dose of BENSPM was compared (80 mg/kg versus 40 mg/kg). The baseline of SSAT activity in the control mice (2 of 7 mice) ranged from 40 to 90 pmol/min/mg. Tumor cells from the human xenografts A121, A549, and HT29 were removed from two mice of each treated group of seven mice containing the respective xenograft at 16 hours following the final BENSPM injection to evaluate the level of induction of SSAT activity. As summarized in Table 9, each of these human carcinoma clonal lines demonstrated significant induction (compared to controls) of SSAT activity. Also, as illustrated in Table 9, accompanying the induction of SSAT in each human xenograft, was a measurable antitumor response. The response to the polyamine analog was heterotypic. For example, the human ovarian carcinoma xenograft (A121) had an antitumor response which differed from that of the human lung (A549) and colon (HT29) carcinoma xenografts. Following polyamine analog treatment, mice containing A121 xenograft showed tumor regression, total growth suppression for a period of 16 days (3.2 times its doubling time), and no regrowth for the duration of the experiment in 2 of 5 mice examined. In contrast, the antitumor response of A549 human xenograft was characterized by no measurable tumor regression and minimal tumor regrowth; however there was a marked growth suppression for 85 days after cessation of treatment (8.5 times doubling time). The antitumor response of HT29 human xenograft was characterized by no measurable tumor regression; however there was a reduced growth rate, and two of five mice examined showed no regrowth for the duration of the experiment. As discussed previously, it is not known whether the heterotypic antitumor response may be due to either the individual properties of the clonal line or the particular solid tumor type. However, as illustrated in Table 9, despite the heterotypic response, a correlation between SSAT induction and a measurable antitumor response was further demonstrated after polyamine treatment of human malignant solid tumor types other than melanoma.

E. Indicia of SSAT induction in extracellular fluid.

Another embodiment of the present invention involves the measurement of the in-vivo induction of SSAT in body fluid rather than from tumor removed from the treated individual. This embodiment relates to the measurement of either $N^1$-acetylspermine levels, $N^1$-acetylspermidine levels, or a combination of both, as measurable indicia of SSAT induction. $N^1$-acetylspermine and $N^1$-acetylspermidine are products of polyamine biosynthesis and back-conversion as illustrated in FIG. 7A. Because $N^1$-acetylspermine and $N^1$-acetylspermidine are rarely found in cells and typically found in the media surrounding cells, it is believed that acetylation represents a signal for export out of cells. Thus, induction of SSAT in a tumor can lead to excretion of acetylated polyamines into surrounding fluids. Depending on the tumor volume and/or the nature of its mileau, acetylated polyamine derivatives can accumulate to measurable levels. For example, acetylated polyamines have been detected in the urine and blood of treated cancer patients, and in some cases, correlated with tumor mass (Abdul-Monem et al., 1978, J. of *Pharm. Sciences*, 67:1671–1673; and Muskiet et al., 1987, *Clin. Chim. Acta* 165:213–225). Thus, acetylated polyamine derivatives may be detected in polyamine analog-treated individuals where SSAT is markedly elevated.

To illustrate this embodiment, LOX and MALME-3 cell cultures were treated for 48 hours with 10 μm BESPM. The cells from each culture were harvested and assayed for SSAT activity. Media samples were prepared by treating the samples with 50% trichloroacetic acid to give a final concentration of 10% and then centrifuged at 15,000×g for 10 minutes. The supernatant was then filtered through a 0.22-μm filter, extracted with several volumes of ether, lyophilized, and resuspended in 10% trichloroacetic acid. $N^1$-acetylspermidine levels of cells and media samples were then measured by use of high-pressure liquid chromatography. As shown in Table 10, $N^1$-acetylspermidine levels from LOX control cells ("intracellular"), media from control cell cultures ("extracellular") and treated LOX cells and media from treated cells contained minimal levels of $N^1$-acetylspermidine. Similarly, $N^1$-acetylspermidine levels from MALME-3 control cells, media from control cell cultures,

TABLE 9

Summary Comparison of BENSPM-Induced SSAT and Antitumor Responses

| Tumor Line (human) | Doubling Time (dt) (days) | SSAT Activity** (pmol/min/mg) | Antitumor Responses (BENSPM at 80 mg/kg 3x/d × 6d)+ | | | |
|---|---|---|---|---|---|---|
| | | | % T/C at 1 g | Tumor Regression | Regrowth Delay | No Regrowth*** |
| A121 | 5 | 2905 | <0 | Present | 3.2 × dt | 2/5 |
| A549 | 10 | 14295 | 13 | None | 8.5 × dt | 2/5 |
| HT29 | 3.5 | 3535 | 24 | None | None | 2/5 |

*After cessation of treatment [times tumor doubling time (dt)]
**Measured 24 hours after final treatment
***For duration of experiment
+Based on median values of at least five mice per group When antitumor response was compared at both 80 mg/kg and 40 mg/kg for these human carcinoma clonal lines, the responses were similar. However, the dose comprising 40 mg/kg appears to be a more defining dose since it provided better separation of the tumor response as indicated by % T/C.

and treated MALME-3 cells contained minimal levels of $N^1$-acetylspermidine. However, media from treated MALME-3 cells exhibited significantly elevated levels of $N^1$-acetylspermidine. As illustrated in Table 10, the elevated levels of $N^1$-acetylspermidine correlate with induction of SSAT measured in the polyamine analog treated MALME-3 cells.

TABLE 10

Excretion of N¹-acetylspermidine in Response to
Induction of SSAT By Polyamine Analog Treatment

| Melanoma (human) | Treatment (48 hours) | SSAT pmol/mg/min | N¹-acetylspermidine Intra-cellular | N¹-acetylspermidine Extra-cellular |
|---|---|---|---|---|
| LOX | Control | 16 | <0.1 | <0.1 |
|  | 10 μm BESPM | 120 | <0.1 | <0.1 |
| MALME-3 | Control | 49 | 0.1 | 0.3 |
|  | 10 μm BESPM | 12,405 | 0.1 | 6.1 |

N¹-acetylspermidine levels expressed as nmol/culture

PREFERRED EMBODIMENTS

The following examples are directed to the measurement of determinants related to the in-vivo induction of SSAT, subsequent to polyamine analog treatment of tumor, which may be used as indica of sensitivity to, therapeutic effectiveness of, and to determine clinically efficacious amounts of, polyamine analogs.

Use of SSAT as a Predictive Assay for Polyamine Analog Therapy

Because the level of induction of SSAT, in response to polyamine analogs such as bis-ethyl spermine analogs, is heterotypic among clonal lines of a specific human tumor type, as well as between different solid tissue types, quantitation of SSAT superinduction could be used in a pretherapy test for evaluating the potential responsiveness of that particular human tumor type to the bis-ethyl spermine analog to be administered. Clinical trials, to establish a range of SSAT induction responses among patients, could be used to further correlate SSAT induction and clinical response to treatment.

EXAMPLE 1

Tumor biopsies or surgical specimens containing tumor may be disaggregated, and introduced into cell culture; or alternatively, grown in culture as explants. Treatment with the polyamine analog such as a bis-ethyl spermine analog is then initiated and continued for up to four cell doublings without medium change. The treated cells are then prepared as cell suspensions for quantitation of SSAT induction.

Embodiment A: SSAT induction can be quantitated by assaying for enzyme activity. Cell extracts of the treated cultured tumor cells may be obtained by sonication, in 5 mMN-2 hydroxy-piperazine-$N^2$-ethane-sulfonic acid (pH 7.2) containing 1 mM dithiothreitol. The cytosolic extract resulting from a 1 hour centrifugation at 35,000 rpm in a Spinco 40 rotor is used as the source of the enzyme for the assay of SSAT activity. The cytosolic extract is incubated with 10 umol HEPES buffer, pHp7.8, 0.15 nmol spermidine, and 0.5 nmol [1-$^{14}$C] acetylCoenzyme A, in a final volume of 50 μl, for 5 minutes at 37° C. The reaction is stopped by chilling, the addition of 20 μl of 0.5 M $NH_2OHCl$, and heating in a boiling water bath for 3 minutes. After centrifugation to remove precipitated protein, 50 μl of the reaction is spotted on a disc of P-81 phosphocellulose and counted for radioactivity. Protein concentration is also measured so that enzyme activity was expressed as picomoles of acetylspermine synthesized per minute per milligram of protein.

Embodiment B: SSAT induction can be quantitated by using a specific antibody to assay for the physical presence of SSAT. In one mode of this embodiment, SSAT may be used as an antigen in immunoassays designed to detect and quantificate SSAT induction. A cell extract or cytosolic extract is prepared as according to the methods in Embodiment A. The detection of SSAT as an antigen in prepared extracts includes any immunoassay system known in the art including, but not limited to: radioimmunoassays, enzyme-linked immunosorbent assays (ELISA), "sandwich" assays, precipitin reactions, agglutination assays, and fluorescent immunoassays.

In another mode of this embodiment, following treatment with a polyamine analog, whole cells can be assayed for the physical presence of SSAT in culture as a monolayer after which an in-situ immunocyto-chemical assay can be performed to detect the presence of an induction of SSAT. This may be quantitated by visual inspection of cell monolayers using a fluorescent microscope, or automatically by fluorescence flow cytometry of a cell suspension prepared from the cell monolayer.

Embodiment C: The basis for the induction of SSAT activity is an induction of enzyme protein related to the combined effects of increased enzyme-specific mRNA (messenger RNA) accumulation, and decreased enzyme protein degradation. Therefore, an alternative to assaying enzyme activity or protein would be to assay for an increase in SSAT-specific m-RNA transcripts. m-RNA can be purified from cell extracts and then subjected to enzymatic amplification to obtain sufficient quantities for analysis and detection. Enzymatic amplification techniques which could be employed include those known in the art such as PCR (polymerase chain reaction), QB replicase, and NASBA (nucleic acid sequence-based amplification). Detection techniques includes systems known in the art including, but not limited to, agarose gel electrophoresis and Northern blotting; fluorescence-based hybridization assays; chemiluminescence-based hybridization assays; and capture hybridization microtiter assays.

Embodiment D: The above procedures and methods of Embodiments A-C would be utilized to measure other indica related to SSAT induction rather than measuring SSAT-specific enzyme activity, protein, or mRNA transcripts. These indica include decreases in the SSAT co-factor acetylCoenzyme A, or increases in SSAT products such as N¹-acetylspermidine and N¹-acetylspermine. Also, mutated or variants of the gene encoding SSAT may be indicative of the potential for SSAT induction.

EXAMPLE 2

Patients having tumor types suspected of being responsive to one or more polyamine analogs, such as bis-ethyl spermine analogs, would be administered a single dose of the analog. Subsequent to this treatment, tumor tissue from the patient would be obtained by biopsy and the tissue may then be subjected to one or more of the methods and procedures outlined in Example 1, Embodiments A-D, for detecting an induction of SSAT.

Use of SSAT as a Tumor Response Marker for Polyamine Analog Treatment

Immediately following bis-ethyl spermine analog treatment, occurs a dramatic increase in SSAT activity. More importantly, the high levels of SSAT activity continue during the sustained growth inhibition following bis-ethyl spermine analog treatment, as exemplified in FIG. 3 with BENSPM treatment. Therefore, the SSAT induction response may serve as a tumor response marker for specifically monitoring the therapeutic effectiveness of bis-ethyl spermine analog treatment, and for determining a dosage regimen and treatment schedule for an individual patient having tumor responsive to bis-ethyl spermine analogs. An indicator useful in determining a dosage regimen and treatment schedule would be particularly desirable in cases where a patient develops adverse side effects as a result of bis-ethyl spermine analog treatment.

Embodiment A: Following treatment with a polyamine analog, and when tumor is conveniently accessible, tumor may be biopsied from the patient. SSAT induction can be quantitated by assaying for enzyme activity. Cell extracts of the biopsied tumor cells may be prepared, and enzyme activity measured, in accordance with the methods and procedures of Example 1, Embodiment A.

Embodiment B: Alternatively, SSAT induction may be quantitated from the biopsied tumor cell extract by using a specific antibody to assay for the physical presence of SSAT according to the methods and procedures of Example 1, Embodiment B. In one mode of this embodiment, SSAT may be used as an antigen in immunoassays designed to detect and quantificate SSAT induction. The detection of SSAT as an antigen in prepared extracts includes any immunoassay system known in the art including, but not limited to: radioimmunoassays; enzyme-linked immunosorbent assays (ELISA); "sandwich" assays; precipitin reactions; agglutination assays; and fluorescent immunoassays.

In another mode of this embodiment, an in-situ cytochemical assay can be performed directly on a histological preparation of the tumor biopsy to detect the presence of an induction of SSAT.

Embodiment C: The basis for the induction of SSAT activity is an induction of enzyme protein related to the combined effects of increased enzyme-specific mRNA (messenger RNA) accumulation, and decreased enzyme protein degradation. Therefore, an alternative to assaying enzyme activity or protein would be to assay for an increase in SSAT-specific m-RNA transcripts as in accordance with the methods and procedures of Example 1, Embodiment C. Systems useful for detecting m-RNA transcripts may be selected from the group consisting of agarose gel electrophoresis and Northern blotting; fluorescence-based hybridization assays; chemiluminescence-based hybridization assays; and capture hybridization microtiter assays.

In another embodiment, the physical presence of SSAT specific mRNA levels can be detected by performing in situ hybridization directly on a histological preparation of the tumor biopsy.

Embodiment D: The above procedures and methods of Embodiments A-C would be utilized to measure other indica related to SSAT induction rather than measuring SSAT-specific enzyme activity, protein, or mRNA transcripts. These indica include decreases in SSAT co-factor acetyl-Coenzyme A, or increases in SSAT products such as $N^1$-acetylspermidine and $N^1$-acetylspermine. Also, mutated or variants of the gene encoding SSAT may be indicative of the potential for SSAT induction.

Embodiment E: Following treatment with a polyamine analog, as an alternative to performing a tumor biopsy from the patient, a blood sample may be drawn, or a urine sample collected. Serum, red blood cell (rbc), or urine levels of SSAT-related products may be selected from the group consisting of $N^1$-acetylspermidine and $N^1$-acetylspermine.

Serum, rbc, or urine levels of these products may be determined using quantitative chromatographic techniques known in the art, such as by HPLC (high pressure liquid chromatography); or an immunoassay system known in the art selected from the group consisting of radioimmunoassays, enzyme-linked immunosorbent assays (ELISA), "sandwich" assays, precipitin reactions, agglutination assays, and fluorescent immunoassays.

Although the present invention has been described in some detail by way of illustration and example for purposes of clarity and understanding, various modifications will become apparent to persons skilled in the art from the foregoing description and accompanying figures. Such modifications are intended to be included within the spirit of this application and within the scope of the appended claims.

What is claimed is:

1. An in vitro method for evaluating the potential responsiveness of a human malignant solid tumor type selected from the group consisting of melanoma, ovarian carcinoma, and lung carcinoma to chemotherapy in vivo with an anti-cancer agent consisting of a polyamine analog selected from the group consisting of spermine analogs and spermidine analogs that induces spermidine/spermine $N^1$-acetyltransferase in said tumor, which comprises the steps of:

(a) performing a biopsy to obtain tumor cells;

(b) introducing cells of said tumor in culture;

(c) administering a therapeutically effective amount of the polyamine analog to the culture; and (d) detecting the level of induction of spermidine/spermine $N^1$-acetyltransferase in the tumor cells exposed to the polyamine analog in vitro;

wherein tumors potentially responsive to polyamine analog chemotherapy are tumors which when exposed to the polyamine analog in vitro show at least a 10 fold induction of spermidine/spermine $N^1$-acetyltransferase relative to untreated tumor of the same clonal line.

2. The method of claim 1, wherein the polyamine analog is a bis-ethyl spermine analog selected from the group consisting of $N^1$, $N^{12}$-bis(ethyl)spermine, $N^1,N^{11}$-bis-(ethyl)norspermine, and $N^1,N^{14}$-bis(ethyl)homospermine, or a combination thereof.

3. The method of claim 1, wherein the induction of spermidine/spermine $N^1$-acetyltransferase is measured by quantifying spermidine/spermine $N^1$-acetyltransferase activity.

4. The method of claim 1, wherein the induction of spermidine/spermine $N^1$-acetyltransferase is measured by assaying for the physical presence of spermidine/spermine $N^1$-acetyltransferase protein.

5. The method of claim 4, wherein the physical presence of using spermidine/spermine $N^1$-acetyltransferase protein as an antigen to be detected in an immunoassay selected from the group consisting of a radioimmunoassay, enzyme-linked immunosorbent assay, "sandwich" assay, precipitin reaction, agglutination assay, fluorescent-based immunoassay, and chemiluminescence-based immunoassay.

6. The method of claim 4, wherein the physical presence of spermidine/spermine $N^1$-acetyltransferase protein is assayed for by an in-situ cytochemical assay specific for spermidine/spermine $N^1$-acetyltransferase.

7. The method of claim 1, wherein the induction of spermidine/spermine $N^1$-acetyltransferase is measured by assaying for spermidine/spermine $N^1$-acetyltransferase m-RNA using a detection technique selected from the group consisting of agarose gel electrophoresis and Northern blotting, fluorescence-based hybridization assay, chemiluminescence-based hybridization assay, and capture hybridization microtiter assay.

8. The method of claim 7, wherein the spermidine/spermine $N^1$-acetyltransferase m-RNA is assayed for in intact cells by in-situ hybridization.

9. The method of claim 7, wherein the spermidine/spermine $N^1$-acetyltransferase m-RNA is first enzymatically amplified.

10. The method of claim 1, wherein the induction of spermidine/spermine $N^1$-acetyltransferase is measured by assaying for a polyamine derivative selected from the group consisting of $N^1$-acetylspermidine, and $N^1$-acetylspermine.

11. The method of claim 1, wherein the induction of spermidine/spermine $N^1$-acetyltransferase is measured by assaying for spermidine/spermine $N^1$-acetyltransferase cofactor acetylCoenzyme A.

12. An in vivo method for evaluating the potential responsiveness of a human malignant solid tumor type selected from the group consisting of melanoma, ovarian carcinoma, and lung carcinoma to chemotherapy with an anticancer agent consisting of a polyamine analog selected from the group consisting of spermine analogs and spermidine analogs that induces spermidine/spermine $N^1$-acetyltransferase in said tumor, which comprises the steps of:

(a) obtaining a sample of untreated tumor of said solid tumor type;

(b) administering a single therapeutic regimen of said polyamine analog to an individual having tumor of said tumor type;

(c) performing a biopsy of the tumor after treatment according to step (b) to obtain treated tumor cells;

(d) detecting in vitro the level of induction of spermidine/spermine $N^1$-acetyltransferase in the treated tumor cells exposed to the polyamine analog within a time period of at least 24 hours after administration, and a basal level of spermidine/spermine $N^1$-acetyltransferase in the untreated tumor;

wherein tumors potentially responsive to polyamine analog chemotherapy in vivo are tumors which when exposed to the polyamine analog in vivo show at least a 30 fold induction of spermidine/spermine $N^1$-acetyltransferase relative to the untreated tumor.

13. The method of claim 12, wherein the polyamine analog is a bis-ethyl spermine analog selected from the group consisting of $N^1$, $N^{12}$-bis(ethyl)spermine, $N^1,N^{11}$-bis-(ethyl)norspermine, and $N^1,N^{14}$-bis(ethyl)homospermine, or a combination thereof.

14. The method of claim 12, wherein the induction of spermidine/spermine $N^1$-acetyltransferase is measured by quantifying spermidine/spermine $N^1$-acetyltransferase activity.

15. The method of claim 12, wherein the induction of spermidine/spermine $N^1$-acetyltransferase is measured by assaying for the physical presence of spermidine/spermine $N^1$-acetyltransferase protein.

16. The method of claim 15, wherein the physical presence of spermidine/spermine $N^1$-acetyltransferase protein is assayed for by using spermidine/spermine $N^1$-acetyltransferase protein as an antigen to be detected in an immunoassay selected from the group consisting of a radioimmunoassay, enzyme-linked immunosorbent assay, "sandwich" assay, precipitin reaction, agglutination assay, fluorescent-based immunoassay, and chemiluminescence-based immunoassay.

17. The method of claim 15, wherein the physical presence of spermidine/spermine $N^1$-acetyltransferase protein is assayed for by an in-situ cytochemical assay specific for spermidine/spermine $N^1$-acetyltransferase.

18. The method of claim 12, wherein the induction of spermidine/spermine $N^1$-acetyltransferase is measured by assaying for spermidine/spermine $N^1$-acetyltransferase m-RNA directly from the tumor cells obtained by biopsy using a detection technique selected from the group consisting of agarose gel electrophoresis and Northern blotting, fluorescence-based hybridization assay, chemiluminescence-based hybridization assay, and capture hybridization microtiter assay.

19. The method of claim 18, wherein the spermidine/spermine $N^1$-acetyltransferase m-RNA is assayed for in intact cells by in-situ hybridization.

20. The method of claim 18, wherein the spermidine/spermine $N^1$-acetyltransferase m-RNA is first enzymatically amplified.

21. The method of claim 12, wherein the induction of spermidine/spermine $N^1$-acetyltransferase is measured by assaying for a polyamine derivative selected from the group consisting of $N^1$-acetylspermidine, and $N^1$-acetylspermine.

22. The method of claim 12, wherein the induction of spermidine/spermine $N^1$-acetyltransferase is measured by assaying for spermidine/spermine $N^1$-acetyltransferase cofactor acetylCoenzyme A.

23. A method for monitoring the therapeutic effectiveness of, and determining a dosage regimen and treatment schedule for, chemotherapy in a mammal having human malignant solid tumor selected from the group consisting of melanoma, ovarian carcinoma, and lung carcinoma responsive to an anticancer agent consisting of a polyamine analog selected from the group consisting of spermine analogs and Spermidine analogs that induces spermidine/spermine $N^1$-acetyltransferase, said method comprising the steps of:

(a) administering a single therapeutic regimen of said polyamine analog to the mammal;

(b) performing a biopsy of the tumor from the mammal to obtain tumor cells; and (c) detecting in vitro the level of induction of spermidine/spermine $N^1$-acetyltransferase in the biopsied tumor cells exposed to polyamine analog chemotherapy.

24. The method of claim 23, wherein the polyamine analog comprises a bis-ethyl spermine analog is selected from the group consisting of $N^1,N^{12}$-bis(ethyl) spermine, $N^1,N^{11}$-bis(ethyl)nor-spermine, and $N^1,N^{14}$-bis(ethyl)homospermine, or a combination thereof.

25. The method of claim 23, wherein the induction of spermidine/spermine $N^1$-acetyltransferase is measured by quantifying spermidine spermine $N^1$-acetyltransferase activity.

26. The method of claim 23, wherein the induction of spermidine/spermine $N^1$-acetyltransferase is measured by assaying for the physical presence of spermidine/spermine $N^1$-acetyltransferase protein.

27. The method of claim 26, wherein the physical presence of spermidine/spermine $N^1$-acetyltransferase protein is assayed for by using spermidine/spermine $N^1$-acetyltransferase protein as an antigen to be detected in an immunoassay selected from the group consisting of a radioimmunoassay, enzyme-linked immunosorbent assay, "sandwich" assay, precipitin reaction, agglutination assay, fluorescent-based immunoassay, and chemiluminescence-based immunoassay.

28. The method of claim 26, wherein the physical presence of spermidine/spermine $N^1$-acetyltransferase protein is assayed for by an in-situ cytochemical assay specific for spermidine/spermine $N^1$-acetyltransferase.

29. The method of claim 23, wherein the induction of spermidine/spermine $N^1$-acetyltransferase is measured by assaying for spermidine/spermine $N^1$-acetyltransferase m-RNA directly from the tumor cells obtained by biopsy using a detection technique selected from the group consisting of agarose gel electrophoresis and Northern blotting, fluorescence-based hybridization assay, chemiluminescence-based hybridization assay, and capture hybridization microtiter assay.

30. The method of claim 29, wherein the spermidine/spermine $N^1$-acetyltransferase m-RNA is assayed for in intact cells by in-situ hybridization.

31. The method of claim 29, wherein the spermidine/spermine $N^1$-acetyltransferase m-RNA is first enzymatically amplified.

32. The method of claim 23, wherein the induction of spermidine/spermine $N^1$-acetyltransferase is measured by assaying for a polyamine derivative selected from the group consisting of $N^1$-acetylspermidine, and $N^1$-acetylspermine.

33. The method of claim 23, wherein the induction of spermidine/spermine $N^1$-acetyltransferase is measured by assaying for spermidine/spermine $N^1$-acetyltransferase cofactor acetylCoenzyme A.

34. A method for monitoring the therapeutic effectiveness of, and determining a dosage regimen and treatment schedule for, chemotherapy in a mammal having human malignant solid tumor selected from the group consisting of melanoma, ovarian carcinoma, and lung carcinoma responsive to an anticancer agent consisting of a polyamine analog selected from the group of consisting of spermine analogs and spermidine analogs that induces spermidine/spermine $N^1$-acetyltransferase, said method comprising the steps of:

(a) administering a single therapeutic regimen of said polyamine analog to the mammal;

(b) collecting body fluid selected from the group of consisting of blood or urine from said mammal; and (c) detecting in vitro an indices of induction of spermidine/spermine $N^1$-acetyltransferase in the body fluid by measuring a polyamine derivative selected from the group consisting of $N^1$-acetylspermidine, and $N^1$-acetylspermine.

35. The method of claim 34, wherein the polyamine analog comprises a bis-ethyl spermine analog is selected from the group consisting of $N^1,N^{12}$-bis(ethyl) spermine, $N^1,N^{11}$-bis(ethyl)nor-spermine, and $N^1,N^{14}$-bis(ethyl)homospermine, or a combination thereof.

* * * * *

UNITED STATES PATENT AND TRADEMARK OFFICE
CERTIFICATE OF CORRECTION

PATENT NO. : 5,498,522
DATED : March 12, 1996
INVENTOR(S) : Carl W. Porter

It is certified that error appears in the above-identified patent and that said Letters Patent is hereby corrected as shown below:

Col. 11, second last line of Table 6 - "158/12" should be --58/12--.

Col. 20, line 52 - after "of" insert --spermidine/spermine $N^1$-acetyltransferase protein is assayed for by--.

Signed and Sealed this

Twenty-third Day of July, 1996

Attest:

BRUCE LEHMAN

Attesting Officer       Commissioner of Patents and Trademarks